United States Patent [19]

Erker et al.

[11] Patent Number: 6,002,032
[45] Date of Patent: Dec. 14, 1999

[54] TRANSITION METAL COMPOUND

[75] Inventors: Gerhard Erker; Bodo Temme, both of Münster; Michael Aulbach, Hofheim; Bernd Bachmann, Eppstein; Frank Küber, Oberursel, all of Germany

[73] Assignee: Targor GmbH, Germany

[21] Appl. No.: 08/478,900

[22] Filed: Jun. 7, 1995

[30] Foreign Application Priority Data

Jun. 13, 1994 [DE] Germany .............................. 44 20 456

[51] Int. Cl.$^6$ ....................................................... C07F 7/08
[52] U.S. Cl. .................. 556/11; 556/27; 556/28; 556/53; 502/152; 502/158; 502/117; 502/155; 502/103; 502/104
[58] Field of Search .................. 556/11, 27, 28, 556/53; 502/152, 158, 117, 155, 103, 104

[56] References Cited

U.S. PATENT DOCUMENTS

| | | |
|---|---|---|
| 5,189,192 | 2/1993 | LaPointe et al. . |
| 5,198,401 | 3/1993 | Turner et al. . |
| 5,241,025 | 8/1993 | Hlatky et al. . |
| 5,527,929 | 6/1996 | Timmers et al. ...................... 556/11 X |
| 5,594,081 | 1/1997 | Uchino et al. ........................... 526/127 |
| 5,631,202 | 5/1997 | Ewen .................................... 556/11 X |
| 5,631,391 | 5/1997 | Canich ...................................... 556/11 |
| 5,633,394 | 5/1997 | Welborn et al. ........................... 556/11 |

FOREIGN PATENT DOCUMENTS

| | | |
|---|---|---|
| 2072058 | 12/1992 | Canada . |
| 1337142 | 9/1995 | Canada . |
| 0 227 004 | 8/1988 | European Pat. Off. . |

OTHER PUBLICATIONS

Van der Linden et al., J.A.C.S., 1995, vol. 117, pp. 3008–3021.
European Search Report No. 95108411, Sep. 27, 1995.
Chemical Abstracts, vol. 119, No. 23, p. 997.Base–free Cationic Mono . . . Olefin Polymerization.
Journal of American Chemical Society, 1995, 117, 3008–3021, Polymerization of Alpha...1–Alkynes.
P. Zdunneck et al., "Über Die Reaktion . . . ", J. Organomet. Chem., 1970, vol. 22, pp. 659–663.
M. Bochmann, "Kationische Alkylkomplexe . . .", Nachr. Chem. Tech. Lab., 1993, vol. 41, pp. 1220–1228.
X. Yang et al., "'Cation–like' Homogeneous . . .", J. Am. Chem. Soc., 1991, vol. 113, 3623–3625.

*Primary Examiner*—Paul F. Shaver
*Attorney, Agent, or Firm*—Connolly Bove Lodge & Hutz LLP

[57] ABSTRACT

The present invention relates to zwitterionic neutral transition metal compounds. The compounds are suitable as catalyst components for the polymerization of olefins.

21 Claims, No Drawings

TRANSITION METAL COMPOUND

The present invention relates to a zwitterionic, neutral transition metal compound which can be advantageously used for the polymerization of olefins. In this way, the use of aluminoxanes such as methylaluminoxane (MAO) as cocatalyst can be omitted while still achieving high catalyst activities.

The role of cationic 14-electron complexes of the formula $R_3M^+$ (M=Ti, Zr, Hf) in Ziegler-Natta polymerization using metallocenes is generally recognized (M. Bochmann, Nachr. Chem. Lab. Techn. 1993, 41, 1220).

While MAO, as the hitherto most effective cocatalyst, has to be used in a high excess, the synthesis of cationic alkyl complexes of the formula $R_3M^+$ (M=Ti, Zr, Hf) provides a route to MAO-free catalysts, some of which have comparable activity.

Cationic alkyl complexes can be prepared by
a) oxidation of metallocene-dialkyl complexes with, for example, $AgBPh_4$ or $[Cp_2Fe][BPh_4]$,
b) by protolysis of metallocene-alkyl compounds with, for example, weakly acid ammonium salts of the very stable, nonbasic tetra(pentafluorophenyl)borate anion (e.g. $[PhMe_2NH]^+[B(C_6F_5)_4]^-$) or by
c) abstraction of an alkyl group from metallocene-alkyl compounds by means of strong Lewis acids. Lewis acids which can be used here are salts $(Ph_3C^+BR_4^-)$ or strong neutral Lewis acids such as $B(C_6F_5)_3$.

J. Organomet. Chem. 1970, 22, 659, describes a reaction of tetramethyltitanium with triphenylborane or tribenzylborane.

J. Am. Chem. Soc. 1991, 113, 3623, describes the synthesis of "cation-like" metallocene polymerization catalysts which are prepared by alkyl abstraction from metallocene-alkyl compounds using tris(pentafluorophenyl)borane. The crystal structure of $[1,2-(CH_3)_2C_5H_3]_2-ZrCH3]^+[CH_3B(C_6F_5)_3]^-$ shows a salt-like structure with weak coordination of the $CH_3$ group of the borate anion to the metal center. EP 427,697 claims this synthetic principle and a corresponding catalyst system comprising a neutral metallocene species (eg. $Cp_2ZrMe_2$), a Lewis acid (eg. $B(C_6F_5)_3$) and aluminum alkyls. EP 520,732 claims a process for preparing salts of the general formula $LMX^+XA^-$ according to the abovedescribed principle.

EP 558,158 claims zwitterionic catalyst systems prepared from metallocene-dialkyl compounds and salts of the formula $[R_3NH]^+[BPh_4]^-$. Reaction of such a salt with $Cp*_2ZrMe_2$ generates, by means of protolysis with elimination of methane, an intermediate zirconocene-methyl cation which reacts, after C—H activation of a tetraphenylborate carbon-hydrogen bond and renewed elimination of methane, to give the zwitterion $Cp*_2Zr^+$-(m-$C_6H_4$)-$B^-Ph_3$. The Zr atom is here covalently bonded to a carbon atom of the phenyl ring and is stabilized via an agostic hydrogen bond. According to this reaction principle, protolysis of a metallocene-dialkyl species with a perfluorinated $[R_3NH]^+[B(C_6F_5)_4]^-$ salt in the first step likewise forms a cationic species, with the subsequent reaction (C—H activation) to give zwitterionic complexes (i.e. the metal atom is covalently bonded to the "former" anion) not being possible. This process also uses metallocenes $CP_2MR_2$ in which the alkyl radicals R are cyclically bonded to one another, for example $Cp_2Zr(2,3$-dimethyl-1,3-butadiene). Salts of the formula $[Cp_2Zr$—R—$RH]^+[B(C_6F_5)_4]^-$ are formed after protonolysis.

U.S. Pat. No. 5,198,401 claims corresponding systems in which dimethylanilinium salts having perfluorinated tetraphenylborate anions are used. This reference also uses metallocenes $Cp_2MR_2$ in which the alkyl radicals R are cyclically bonded to one another, for example $Cp_2Zr$-(2,3-dimethyl-1,3-butadiene). After protonolysis, salts of the formula $[Cp_2Zr$—R—$RH]^+[B(C_6F_5)_4]^-$ are likewise formed. EP 277,003, EP 277,004, EP 495,375 and WO 91/14713 claim systems according to a similar process principle.

The processes described for preparing the cationic systems of the formula $[R_3M]^+[BR_4]^-$ (M=Ti, Zr, Hf) have the disadvantage that the cationizing reagents $[R_3NH^+BR_4^-]$ are sometimes complicated to synthesize and costly. In addition, there is the problem that an amine $R_3N$ is formed from the ammonium salt after protonolysis, which amine, in the case of sterically unhindered metal centers, can coordinate to the strong Lewis acid $R_3M^+$ cation (U.S. Pat. No. 5,198,401) and thus leads to low polymerization activities.

The zwitterionic complexes of the structure $Cp_2Zr^+$-m-$C_6H_4B^-Ph_3$ have the disadvantage that the starting compounds are expensive and complicated to synthesize and have low polymerization activity.

Owing to their salt-like character, cationic systems of the structure $[Cp_2MR]^+[RB(C_6F_5)_3]^-$ have very high hydrolysis sensitivities and can be used on an industrial scale only to a limited extent. The activities observed for these systems are low owing to the abovementioned stability problems and the presumably sometimes strong coordination of the alkyl group of the borate anion to the metal center.

It is an object of the invention to find a transition metal compound which avoids the disadvantages of the prior art.

It has now been found that this object can be achieved by specific zwitterionic transition metal compounds.

The present invention accordingly provides a zwitterionic transition metal compound of the formula I

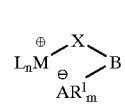

(I)

where

L are identical or different and are each a π-ligand or an electron donor, n is equal to 1, 2, 3 or 4, M is a metal atom of group IIIb, IVb, Vb or VIb of the Periodic Table of the Elements, X is a heteroatom or a hydrocarbon group having 1–40 carbon atoms, B is a hydrocarbon group having 1–40 carbon atoms, A is a metal atom of group Ib, IIb, IIIa, IIIb, IVa, Va, Vb, VIb, VIIb or VIIIb of the Periodic Table of the Elements, $R^1$ are identical or different and are each a perhalogenated $C_1$–$C_{40}$-hydrocarbon radical, and m is equal to 1, 2, 3, 4 or 5.

The metal atoms M and A bonded to one another by covalent bonds via the structural elements X and B. If X is an allyl unit, the bonding of X to the metal atom X can be a σ-allyl or a π-allyl bond. π-Ligands are preferably unsubstituted or substituted cyclopentadienyl groups such as 2-methylcyclopentadienyl, indenyl, 2-methylindenyl, 2-methyl-4-phenylindenyl, 2-methyl-4,5-benzoindenyl, 2-methyl-4,6-diisopropylindenyl, 4,5-benzoindenyl, fluorenyl, 4,7-tert-butylfluorenyl or 2-methyl-4-(2-pyridyl) indenyl.

For the purposes of the present invention, an electron donor is an atom of group IVa, Va, VIa or VIIa of the Periodic Table of the Elements, which can bear substituents such as $C_1$–$C_{20}$-hydrocarbon groups. Preference is given to O, $NR^4{}_2$, $NR^4$, $NR^4{}_3$, $PR^4{}_2$, $PR^4$, $PR^4{}_3$, S, $P(OR^4)_2$, $P(OR^4)$ or Cl, where $R^4$ is $C_1$–$C_{20}$-alkyl or $C_6$–$C_{14}$-aryl.

Two radicals L can be linked to one another via a bridge (Z).

The bridge Z is preferably

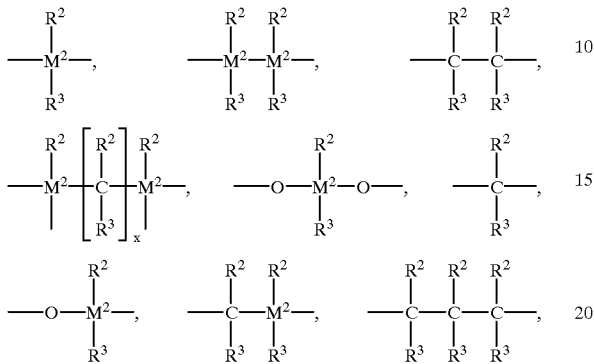

=$BR_2$, —$AlR^2$, —Ge—, —O—, —S—, =SO, =$SO_2$, —$NR_2$, =CO, =$PR^2$ or =$P(O)R^2$, where $R^2$ and $R^3$ are identical or different and are each a hydrogen atom, a halogen atom, a $C_1$–$C_{20}$-alkyl group, a $C_1$–$C_1$-fluoroalkyl group, a $C_1$–$C_{10}$-alkoxy group, a $C_6$–$C_{14}$-aryl group, a $C_6$–$C_{10}$-fluoroaryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group and x is a number from zero to 18, or $R^2$ and $R^3$ together with the atoms-connecting them form one or more rings and $R^2$ or/and $R^3$ can be bonded to L and $M^2$ is silicon, germanium or tin.

Z can also link two or more identical or different groups $L_nM^+XBA^-R^1{}_m$ with one another.

For the purposes of the present invention, a heteroatom is any atom of the Periodic Table of the Elements with the exceptions of carbon and hydrogen. Preference is given to O, S and N.

Hydrocarbon groups X and B can be saturated or unsaturated, linear or branched, eg. a $C_1$–$C_{20}$-alkyl group, a $C_6$–$C_{14}$-aryl group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group. Preference is given to substituted or unsubstituted alkyl groups which can also have aromatic structural elements.

Preference is given to n=1 when M is an element of group IIIb of the Periodic Table of the Elements; n=2 when M is a metal atom of group IVb of the Periodic Table of the Elements; n=3 when M is an element of group Vb of the Periodic Table of the Elements; and n=4 when M is an element of group VIb of the Periodic Table of the Elements.

$R^1$ is a $C_1$–$C_{40}$-hydrocarbon radical which is perhalogenated with halogen such as fluorine, chlorine, bromine or iodine, in particular a perhalogenated $C_1$–$C_{30}$-alkyl group such as trifluoromethyl, pentachloroethyl, heptafluoroisopropyl, or monofluoroisobutyl or a perhalogenated $C_6$–$C_{30}$-aryl group such as pentafluorophenyl, heptachloronaphthyl, heptafluoronaphthyl or heptafluorotolyl.

Particular preference is given to compounds of the formula I, where

M is a metal atom of group IVb of the Periodic Table of the Elements, such as titanium, zirconium or hafnium, n is equal to 2, L are identical or different and are each a substituted or unsubstituted cyclopentadienyl group, where two radicals L can be linked to one another via a bridge Z and Z is $CR^2R^3$ or $SiR^2R^3$ or a unit Si—$(CR^2R^3)_x$—Si which links two fragments $L_nM^+XBA$-$R^1{}_m$ with one another, where x is an integer from 0 to 10, preferably x=6, X and B together form a three-membered to five-membered ($C_3$–$C_5$)-alkyl chain which is saturated or unsaturated and can be substituted by $C_1$–$C_{20}$-hydrocarbon radicals, A is a metal of group Ib, IIb, IIIa, IVa, Va, Vb of the Periodic Table of the Elements, $R^1$ are identical or different and are each a perfluorinated alkyl or aryl group having from 1 to 20 carbon atoms and m is equal to 2, 3 or 4.

Very particular preference is given to compounds of the formula I, where

M is zirconium, n is equal to 2,

L are identical or different and are each a substituted cyclopentadienyl group, where two radicals L are bonded to one another via a bridge Z, where Z is $CR^2R^3$ or $SiR^2R^3$, X and B together form an unsaturated four-membered ($C_4$)-alkyl chain whose hydrogen atoms can also be replaced by $C_1$–$C_{20}$-alkyl groups, A is a boron atom, $R^1$ are identical and are each a pentafluorophenyl group ($C_6F_5$) and m is equal to 3.

Examples of compounds of the invention are:
bis(cyclopentadienyl)$Zr^+CH_2CHCHCH_2B^-(C_6F_5)_3$;
bis(methylcyclopentadienyl)$Zr^+C_2CHCHCH_2B^-(C_6F_5)_3$;
bis(n-butylcyclopentadienyl)$Zr^+CH_2CHCHCH_2B^-(C_6F_5)_3$;
bisindenyl$Zr^+CH_2CHCHCH_2B^-(C_6F_5)_3$;
(tert-butylamido)dimethyl(tetramethyl-$\eta^5$-cyclopentadienyl)silane$Zr^+CH_2CHCHCH_2B^-(C_6F_5)_3$;
bis(2-methylbenzoindenyl)$Zr^+CH_2CHCHCH_2B^-(C_6F_5)_3$;
dimethylsilanediylbis(2-methylindenyl)$Zr^+$ $CH_2CHCHCH_2B^-(C_6F_5)_3$;
dimethylsilanediylbisindenyl$Zr^+CH_2CHCHCH_2B^-(C_6F_5)_3$;
dimethylsilanediylbis(2-methylbenzoindenyl)$Zr^+$ $CH_2CHCHCH_2B^-(C_6F_5)_3$;
dimethylsilanediyl(2-methylbenzoindenyl)(2-methylindenyl)$Zr^{+CH}{}_2CHCHCH_2B^-(C_6F_5)_3$;
dimethylsilanediyl(2-methylbenzoindenyl)(2-methyl-4-phenylindenyl)$Zr^+CH_2$ $CHCHCH_2B$ $(C_6F_5)_3$;
dimethylsilanediyl(2-methylindenyl)(4-phenylindenyl)$Zr^+$ $CH_2CHCHCH_2B^-(C_6F_5)_3$;
dimethylsilanediylbis(2-methyl-4-phenylindenyl)$Zr^+$ $CH_2CHCHCH_2B^-(C_6F_5)_3$;
dimethylsilanediylbis(2-methyl-4,6-diisopropylindenyl)$Zr^+$ $CH_2CHCHCH_2B^-(C_6F_5)_3$;
dimethylsilanediylbis(2-methyl-4-naphthylindenyl)$Zr^+$ $CH_2CHCHCH_2B^-(C_6F_5)_3$;
isopropylidene(cyclopentadienyl)(fluorenyl)$Zr^+$ $CH_2CHCHCH_2B^-(C_6F_5)_3$;
isopropylidene(cyclopentadienyl)(indenyl)$Zr^+$ $CH_2CHCHCH_2B^-(C_6F_5)_3$;
[4-$\eta^5$-cyclopentadienyl-4,7,7-trimethyl-($\eta^5$-4,5,6,7-tetrahydroindenyl)$Zr^+CH_2CHCHCH_2B^-(C_6F_5)_3$;
dimethylsilanediylbis(2-methylindenyl)$Zr^+$ $OCH_2CH_2CH_2B^-(C_6F_5)_3$;
dimethylsilanediylbisindenyl$Zr^+OCH_2CH_2CH_2B^-(C_6F_5)_3$;

dimethylsilanediylbis(2-methylbenzoindenyl)Zr$^+$ OCH$_2$CH$_2$CH$_2$B$^-$(C$_6$F$_5$)$_3$;
dimethylsilanediyl(2-methylbenzoindenyl)(2-methylindenyl)Zr$^+$OCH$_2$CH$_2$CH$_2$B$^-$(C$_6$F$_5$)$_3$;
dimethylsilanediyl(2-methylbenzoindenyl)(2-methyl-4-phenylindenyl)Zr$^+$OCH$_2$CH$_2$CH$_2$B$^-$(C$_6$F$_5$)$_3$;
dimethylsilanediyl(2-methylindenyl)(4-phenylindenyl)Zr$^+$ OCH$_2$CH$_2$CH$_2$B$^-$(C$_6$F$_5$)$_3$;
dimethylsilanediylbis(2-methyl-4-phenylindenyl)Zr$^+$ OCH$_2$CH$_2$CH$_2$B$^-$(C$_6$F$_5$)$_3$;
dimethylsilanediylbis(2-methyl-4,6-diisopropylindenyl)Zr$^+$ OCH$_2$CH$_2$CH$_2$B$^-$(C$_6$F$_5$)$_3$;
dimethylsilanediylbis(2-methylindenyl)Zr$^+$ CH$_2$CHCHCH$_2$B$^-$(CF$_3$)$_3$;
dimethylsilanediylbisindenylZr$^+$CH$_2$CHCHCH$_2$B$^-$(CF$_3$)$_3$;
dimethylsilanediylbis(2-methylbenzoindenyl)Zr$^+$ CH$_2$CHCHCH$_2$B$^-$(CF$_3$)$_3$;
dimethylsilanediyl(2-methylbenzoindenyl)(2-methylindenyl)Zr$^+$CH$_2$CHCHCH$_2$B$^-$(CF$_3$)$_3$;
dimethylsilanediyl(2-methylbenzoindenyl)(2-methyl-4-phenylindenyl)Zr$^+$CH$_2$CHCHCH$_2$B$^-$(CF$_3$)$_3$;
dimethylsilanediyl(2-methylindenyl)(4-phenylindenyl)Zr$^+$ CH$_2$CHCHCH$_2$B$^-$(CF$_3$)$_3$;
dimethylsilanediylbis(2-methyl-4-phenylindenyl)Zr$^+$ CH$_2$CHCHCH$_2$B$^-$(CF$_3$)$_3$;
dimethylsilanediylbis(2-methyl-4,6-diisopropylindenyl)Zr$^+$ CH$_2$CHCHCH$_2$B$^-$(CF$_3$)$_3$;
dimethylsilanediylbis(2-methyl-4-naphthylindenyl)Zr$^+$ CH$_2$CHCHCH$_2$B$^-$(CF$_3$)$_3$;
dimethylsilanediylbis(2-methylindenyl)Zr$^+$CH$_2$C(CH$_3$)C(CH$_3$)CH$_2$B$^-$(CF$_3$)$_3$;
dimethylsilanediylbisindenylZr$^+$CH$_2$C(CH$_3$)C(CH$_3$)CH$_2$B$^-$(CF$_3$)$_3$;
dimethylsilanediylbis(2-methylbenzoindenyl)Zr$^+$CH$_2$C(CH$_3$)C(CH$_3$)CH$_2$B$^-$(CF$_3$)$_3$;
dimethylsilanediyl(2-methylbenzoindenyl)(2-methylindenyl)Zr$^+$CH$_2$C(CH$_3$)C(CH$_3$)CH$_2$B$^-$(CF$_3$)$_3$;
dimethylsilanediyl(2-methylbenzoindenyl)(2-methyl-4-phenylindenyl)Zr$^+$CH$_2$C(CH$_3$)C(CH$_3$)CH$_2$B$^-$(CF$_3$)$_3$;
dimethylsilanediyl(2-methylindenyl)(4-phenylindenyl)Zr$^+$ CH$_2$C(CH$_3$)C(CH$_3$)CH$_2$B$^-$(CF$_3$)$_3$;
dimethylsilanediylbis(2-methyl-4-phenylindenyl)Zr$^+$CH$_2$C(CH$_3$)C(CH$_3$)CH$_2$B$^-$(CF$_3$)$_3$;
dimethylsilanediylbis(2-methyl-4,6-diisopropylindenyl)Zr$^+$ CH$_2$C(CH$_3$)C(CH$_3$)CH$_2$B$^-$(CF$_3$)$_3$;
dimethylsilanediylbis(2-methyl-4-naphthylindenyl)Zr$^+$ CH$_2$C(CH$_3$)C(CH$_3$)CH$_2$B$^-$(CF$_3$)$_3$;
methylphenylmethylene(fluorenyl)(cyclopentadienyl)Zr$^+$ CH$_2$CHCHCH$_2$B$^-$(C$_6$F$_5$)$_3$;
diphenylmethylene(fluorenyl)(cyclopentadienyl)Zr$^+$ CH$_2$CHCHCH$_2$B$^-$(C$_6$F$_5$)$_3$;
isopropylidene(3-methylcyclopentadienyl)(fluorenyl)Zr$^+$ CH$_2$CHCHCH$_2$B$^-$(C$_6$F$_5$)$_3$;
dimethylsilanediyl(3-tert-butylcyclopentadienyl)(fluorenyl) Zr$^+$CH$_2$CHCHCH$_2$B$^-$(C$_6$F$_5$)$_3$;
diphenylsilanediyl(3-(trimethylsilyl)cyclopentadienyl) (fluorenyl)Zr$^+$CH$_2$CHCHCH$_2$B$^-$(C$_6$F$_5$)$_3$;
phenylmethylsilanediylbis(2-methylindenyl)Zr$^+$ CH$_2$CHCHCH$_2$B$^-$(C$_6$F$_5$)$_3$;
phenylmethylsilanediylbisindenylZr$^+$CH$_2$CHCHCH$_2$B$^-$(C$_6$F$_5$)$_3$;
phenylmethylsilanediylbis(2-methyl-4,5-benzoindenyl)Zr$^+$ CH$_2$CHCHCH$_2$B$^-$(C$_6$F$_5$)$_3$;
phenylmethylsilanediyl(2-methyl-4,5-benzoindenyl)(2-methylindenyl)Zr$^+$CH$_2$CHCHCH$_2$B$^-$(C$_6$F$_5$)$_3$;
phenylmethylsilanediyl(2-methyl-4,5-benzoindenyl)(2-methyl-4-phenylindenyl)Zr$^+$CH$_2$CHCHCH$_2$B$^-$(C$_6$F$_5$)$_3$;
phenylmethylsilanediyl(2-methylindenyl)(4-phenylindenyl) Zr$^+$CH$_2$CHCHCH$_2$B$^-$(C$_6$F$_5$)$_3$;
phenylmethylsilanediylbis(2-methyl-4-phenylindenyl)Zr$^+$ CH$_2$CHCHCH$_2$B$^-$(C$_6$F$_5$)$_3$;
phenylmethylsilanediylbis(2-ethyl-4-phenylindenyl)Zr$^+$ CH$_2$CHCHCH$_2$B$^-$(C$_6$F$_5$)$_3$;
phenylmethylsilanediylbis(2-methyl-4,6-diisopropylindenyl)Zr$^+$CH$_2$CHCHCH$_2$B$^-$(C$_6$F$_5$)$_3$;
phenylmethylsilanediylbis(2-methyl-4-naphthylindenyl)Zr$^+$ CH$_2$CHCHCH$_2$B$^-$(C$_6$F$_5$)$_3$;
ethylenebis(2-methylindenyl)Zr$^+$CH$_2$CHCHCH$_2$B$^-$(C$_6$F$_5$)$_3$;
ethylenebisindenylZr$^+$CH$_2$CHCHCH$_2$B$^-$(C$_6$F$_5$)$_3$;
ethylenebis(2-methyl-4,5-benzoindenyl)Zr$^+$ CH$_2$CHCHCH$_2$B$^-$(C$_6$F$_5$)$_3$;
ethylene(2-methyl-4,5-benzoindenyl)(2-methylindenyl)Zr$^+$ CH$_2$CHCHCH$_2$B$^-$(C$_6$F$_5$)$_3$;
ethylene(2-methyl-4,5-benzoindenyl)(2-methyl-4-phenylindenyl)Zr$^+$CH$_2$CHCHCH$_2$B$^-$(C$_6$F$_5$)$_3$;
ethylene(2-methylindenyl)(4-phenylindenyl)Zr$^+$ CH$_2$CHCHCH$_2$B$^-$(C$_6$F$_5$)$_3$;
ethylenebis(2-methyl-4,5-benzoindenyl)Zr$^+$ CH$_2$CHCHCH$_2$B$^-$(C$_6$F$_5$)$_3$;
ethylenebis(2-methyl-4-phenylindenyl)Zr$^+$ CH$_2$CHCHCH$_2$B$^-$(C$_6$F$_5$)$_3$;
ethylenebis(2-methyl-4,6-diisopropylindenyl)Zr$^+$ CH$_2$CHCHCH$_2$B$^-$(C$_6$F$_5$)$_3$;
ethylenebis(2-methyl-4-naphthylindenyl)Zr$^+$ CH$_2$CHCHCH$_2$B$^-$(C$_6$F$_5$)$_3$;
ethylenebis(2-ethyl-4-phenylindenyl)Zr$^+$CH$_2$CHCHCH$_2$B$^-$(C$_6$F$_5$)$_3$;
ethylenebis(2-ethyl-4,6-diisopropylindenyl)Zr$^+$ CH$_2$CHCHCH$_2$B$^-$(C$_6$F$_5$)$_3$;
ethylenebis(2-ethyl-4-naphthylindenyl)Zr$^+$ CH$_2$CHCHCH$_2$B$^-$(C$_6$F$_5$)$_3$;
dimethylsilanediylbis(2-ethyl-4-phenylindenyl)Zr$^+$ CH$_2$CHCHCH$_2$B$^-$(C$_6$F$_5$)$_3$;
dimethylsilanediylbis(2,3,5-trimethylcyclopentadienyl)Zr$^+$ CH$_2$CHCHCH$_2$B$^-$(C$_6$F$_5$)$_3$;
1,6-{bis[methylsilylbis(2-methyl-4-phenylindenyl)Zr$^+$ CH$_2$CHCHCH$_2$B$^-$(C$_6$F$_5$)$_3$]}hexane;
1,6-{bis[methylsilylbis(2-ethyl-4-phenylindenyl)Zr$^+$ CH$_2$CHCHCH$_2$B$^-$(C$_6$F$_5$)$_3$]}hexane;
1,6-{bis[methylsilylbis(2-methyl-4-naphthylindenyl)Zr$^+$ CH$_2$CHCHCH$_2$B$^-$(C$_6$F$_5$)$_3$]}hexane;
1,6-{bis[methylsilylbis(2-methyl-4,5-benzoindenyl)Zr$^+$ CH$_2$CHCHCH$_2$B$^-$(C$_6$F$_5$)$_3$]}hexane;
1,6-{bis[methylsilyl(2-methyl-4-phenylindenyl)(2-methylindenyl)Zr$^+$CH$_2$CHCHCH$_2$B$^-$(C$_6$F$_5$)$_3$]}hexane;
1,2-{bis[methylsilylbis(2-methyl-4-phenylindenyl)Zr$^+$ CH$_2$CHCHCH$_2$B$^-$(C$_6$F$_5$)$_3$]}ethane;
1,2-{bis[methylsilylbis(2-ethyl-4-phenylindenyl)Zr$^+$ CH$_2$CHCHCH$_2$B$^-$(C$_6$F$_5$)$_3$]}ethane;
1,2-{bis[methylsilylbis(2-methyl-4-naphthylindenyl)Zr$^+$ CH$_2$CHCHCH$_2$B$^-$(C$_6$F$_5$)$_3$]}ethane;
1,2-{bis[methylsilylbis(2-methyl-4,5-benzoindenyl)Z$^+$ CH$_2$CHCHCH$_2$B$^-$(C$_6$F$_5$)$_3$]}ethane;
1,2-{bis[methylsilyl(2-methyl-4-phenylindenyl)(2-methylindenyl)Zr$^+$CH$_2$CHCHCH$_2$B$^-$(C$_6$F$_5$)$_3$]}ethane.

The preparation of the novel transition metal compound of the formula I is illustrated by the following reaction schemes.

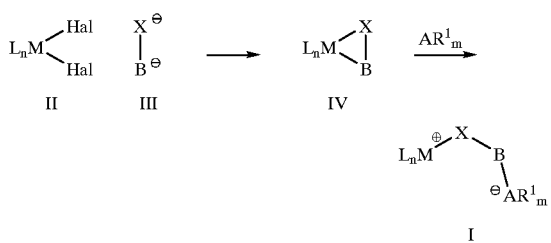

L, n, M, X, B, A, $R^1$ and m in the formulae II, III and IV are as defined in formula I and Hal is a halogen atom such as fluorine, chlorine, bromine or iodine.

Compounds of the formula II are described in the literature (J. Okuda, Topics in Current Chemistry, Vol. 160; Springer Verlag, Berlin Heidelberg 1991, page 97). Reaction of compounds of the formula II in inert solvents with dianion compounds of the formula III, for example 1,4-butanediyllithium or 2-butene-1,4-diylmagnesium, leads to elimination of a salt and formation of the cyclic systems IV in which the M—X or the M—B bond can be a covalent bond or a coordination of the compound X—B to the metal atom M.

The compound of the formula IV can be reacted with Lewis acids of the formula $AR^1_m$ in organic solvents, for example toluene, benzene, methylene chloride, carbon tetrachloride and petroleum spirit, to give the compound of the formula I.

The novel transition metal compounds of the formula I can be isolated or directly used for further reactions. The compounds of the formula I can also be prepared without isolation of intermediate and end stages in a single-vessel reaction from metallocene dihalides, dianion compounds and Lewis acids and be directly used for the polymerization.

Suitable solvents for this purpose are aliphatic or aromatic solvents, such as hexane or toluene, or halogenated hydrocarbons, such as methylene chloride, or halogenated aromatic hydrocarbons such as o-dichlorobenzene.

A further possibility for preparing the novel compounds of the formula I comprises the formation of metallocycles of the formula IV by electrocyclic ring-closure reaction of, for example, metallocene-bisolefin complexes or metallocene-olefin-aldehyde complexes and subsequent reaction with $Ar^1_m$.

The present invention also relates to a process for preparing an olefin polymer by polymerization of at least one olefin in the presence of a catalyst containing at least one transition metal compound of the formula I. The polymerization can be a homopolymerization or a copolymerization.

Preference is given to polymerizing olefins of the formula $R^a$—CH=CH—$R^b$, where $R^a$ and $R^b$ are identical or different and are each a hydrogen atom, a halogen atom, an alkoxy group, a hydroxy group, an alkylhydroxy group, an aldehyde group, a carboxylic acid group or a carboxylic ester group or a saturated or unsaturated hydrocarbon radical having from 1 to 20 carbon atoms, in particular from 1 to 10 carbon atoms, which can be substituted by an alkoxy group, a hydroxy group, an alkylhydroxy group, an aldehyde group, a carboxylic acid group or a carboxylic ester group, or $R^a$ and $R^b$ together with the atoms connecting them can form a one or more rings. Examples of such olefins are 1-olefins such as ethylene, propylene, 1-butene, 1-hexene, 4-methyl-1-pentene, 1-octene, styrene, cyclic olefins such as norbornene, vinylnorbornene, tetracyclododecene, ethylidenenorbornene, dienes such as 1,3-butadiene or 1,4-hexadiene, biscyclopentadiene or methyl methacrylate. In particular, propylene or ethylene are homopolymerized, ethylene is copolymerized with one or more $C_3$–$C_{20}$-1-olefins, in particular propylene, and/or one or more $C_4$–$C_{20}$-dienes, in particular 1,3-butadiene, or norbornene and ethylene are copolymerized.

The polymerization is preferably carried out at a temperature of from −60 to 300° C., particularly preferably from 30 to 250° C. The pressure is from 0.5 to 2500 bar, preferably from 2 to 1500 bar. The polymerization can be carried out continuously or batchwise, in one or more stages, in solution, in suspension, in the gas phase or in a supercritical medium.

It is also possible to use mixtures of two or more transition metal compounds of the formula I. By this means, polyolefins having a broad or multimodal molecular weight distribution can be obtained.

A prepolymerization can be carried out by means of the compound of the formula I. For the prepolymerization, preference is given to using the (or one of the) olefin(s) used in the polymerization.

The compounds of the formula I can also be applied to a support, particularly for controlling the particle morphology. Suitable support materials are, for example, silica gels, aluminum oxides, solid aluminoxane or other inorganic support materials such as, for example, magnesium chloride. Another suitable support material is a polyolefin powder in finely divided form.

The supported catalyst system can be resuspended as powder or still together with solvent and can be metered into the polymerization system as a suspension in an inert suspension medium.

To remove catalyst poisons present in the olefin, purification using an aluminum alkyl, for example trimethylaluminum, triethylaluminum or triisobutylaluminum, is advantageous. This purification can be carried out either in the polymerization system itself or the olefin is contacted with the Al compound and subsequently separated again prior to its addition to the polymerization system.

Hydrogen is added, if required, as molecular weight regulator and/or to increase the activity. The total pressure in the polymerization system is from 0.5 to 2500 bar, preferably from 2 to 1500 bar.

The compound of the formula I is here used in a concentration, based on the transition metal, of preferably from $10^{-3}$ to $10^{-8}$, particularly preferably from $10^{-4}$ to $10^{-7}$, mol of transition metal per $dm^3$ of solvent or per $dm^3$ of reactor volume.

If the polymerization is carried out as a suspension or solution polymerization, an inert solvent customary for the Ziegler low-pressure process is used. For example, the polymerization is carried out in an aliphatic or cycloaliphatic hydrocarbon; examples of such solvents which may be mentioned are propane, butane, hexane, heptane, isooctane, cyclohexane, methylcyclohexane. Furthermore, a petroleum or hydrogenated diesel oil fraction can be used. It is also possible to use toluene. Preference is given to carrying out the polymerization in the liquid monomer.

If inert solvents are used, the monomers are metered in in gaseous or liquid form.

The duration of the polymerization can be as desired, since the catalyst system to be used according to the invention has only a small fall in polymerization activity with time.

Prior to addition of the catalyst, in particular the supported catalyst system (containing at least one novel compound of the formula I, support material and/or a polyolefin powder in finely divided form), another aluminum alkyl compound such as, for example, trimethylaluminum, triethylaluminum, triisobutylaluminum, trioctylaluminum or isoprenylaluminum can additionally be added to the reactor to stabilize the polymerization system (for example for removing catalyst poisons present in the olefin). This is added to the polymerization system in a concentration of from 100 to 0.01 mmol of Al per kg of reactor contents. Preference is given to triisobutylaluminum and triethylaluminum in a concentration of from 10 to 0.1 mmol of Al per kg of reactor contents. This enables a small Al/M molar ratio to be selected in the synthesis of a supported catalyst system.

The novel compounds of the formula I are highly active catalyst components for olefin polymerization.

In principle, the use of cocatalysts in the polymerization reaction is not required, i.e. the novel compounds of the formula I can be used as catalyst for olefin polymerization without the need for a cocatalyst such as aluminoxane.

The following examples serve to illustrate the invention.

General procedures: Preparation and handling of organometallic compounds were carried out with exclusion of air and moisture under argon protection (Schlenk technique). All solvents required were dried prior to use by boiling for a number of hours over a suitable desiccant and subsequent distillation.

The compounds were characterized using $^1$H-NMR, $^{13}$C-NMR and IR spectroscopy.

A. Synthesis of the Compounds of the Formula IV

The preparation of the butadiene complexes was carried out according to G. Erker, K. Engel, Ch. Sarter in R. B. King, J. J. Eisch, Organometallic Synthesis, Vol 3, Academic Press, New York 1986, 529:

EXAMPLE 1

Dimethylsilanediylbis(2-methyl-4,5-benzoindenyl) zirconium($\eta^4$-butadiene)

100 ml of toluene (precooled to −40° C.) are added to a mixture of 5.0 g (8.67 mmol) of dimethylsilanediylbis(2-methyl-4,5-benzoindenyl)zirconium dichloride and 2.3 g (10.4 mmol, 1.2 equivalents) of (2-butene-1,4-diyl) magnesium bistetrahydrofuran ("butadienemagnesium") which has been cooled to −40° C. While stirring vigorously, the mixture is allowed slowly to warm up to room temperature. After stirring for four hours, the dark red solution is separated via a frit from unreacted butadienemagnesium and magnesium chloride formed. The filtrate is evaporated to dryness and the residue is washed with 10 ml of pentane. This gives 4.4 g (70%) of a deep red powder.

EXAMPLE 2

Dimethylsilanediylbis(2-methyl-4-phenylindenyl) zirconium($\eta^4$-butadiene)

100 ml of toluene (precooled to −40° C.) are added to a mixture of 5.0 g (7.95 mmol) of dimethylsilanediylbis(2-methyl-4-phenylindenyl)zirconium dichloride and 2.1 g (9.5 mmol, 1.2 equivalents) of (2-butene-1,4-diyl)magnesium bistetrahydrofuran ("butadienemagnesium") which has been cooled to −40° C. While stirring vigorously, the mixture is allowed slowly to warm up to room temperature. After stirring for four hours, the dark red solution is separated via a frit from unreacted butadienemagnesium and magnesium chloride formed. The filtrate is evaporated to dryness and the residue is washed with 10 ml of pentane. This gives 3.5 g (72%) of a red-brown powder.

B. Synthesis of the Compounds of the Formula I

EXAMPLE 3

Dimethylsilanediylbis(2-methyl-4,5-benzoindenyl) $Zr^+CH_2CHCHCH_2B^-(C_6F_5)_3$;

3.0 g (5.35 mmol) of dimethylsilanediylbis(2-methyl-4,5-benzoindenyl)zirconium($\eta^4$-butadiene) are dissolved in 100 ml of toluene and admixed with 3.01 g (5.88 mmol, 1.1 equivalents) of tris(pentafluorophenyl)borane. The reaction solution is left stirring for 24 hours at room temperature and the strongly dark brown suspension is subsequently evaporated to half its volume. The precipitate is filtered off and washed with 10 ml of pentane. This gives 5.27 g (92%) of a sparingly soluble reddish brown powder.

EXAMPLE 4

Dimethylsilanediylbis(2-methyl-4-phenylindenyl) $Zr^+CH_2CHCHCH_2B^-(C_6F_5)_3$;

3.0 g (4.90 mmol) of dimethylsilanediylbis(2-methyl-4-phenylindenyl)zirconium($\eta^4$-butadiene) are dissolved in 100 ml of toluene and admixed with 2.76 g (5.39 mmol, 1.1 equivalents) of tris(pentafluorophenyl)borane. The reaction solution is left stirring for 24 hours at room temperature and the strongly dark brown suspension is subsequently evaporated to half its volume. The precipitate is filtered off and washed with 10 ml of pentane. This gives 4.84 g (88%) of a sparingly soluble reddish brown powder.

C. Polymerization Examples

EXAMPLE 5

The catalyst solution is prepared by mixing 11 mg of biscyclopentadienylzirconium($\eta^4$-butadiene) in 20 ml of toluene with a solution of 20.4 mg of tris(pentafluorophenyl) borane in 20 ml of toluene. 900 ml of toluene are admixed with 1 ml of a 10% strength by weight TIBA solution in toluene and subsequently with 1 ml of this catalyst solution.

For the polymerization, this solution is placed in an inert 1.5 dm$^3$ stirred reactor, heated to 70° C. and polymerization is carried out at a pressure of 7 bar of ethylene. After 2 hours, the reactor is vented, the polymer is filtered from the suspension, washed with acetone and dried for 12 hours in a vacuum drying oven. This gives 38 g of polyethylene having an $M_w$ of 297,000 g/mol and an $M_w/M_n$ of 2.5 according to GPC.

EXAMPLE 6

The polymerization of Example 5 is repeated using high-purity ethylene, except that no TIBA was added. This gives 37 g of polyethylene having identical properties.

EXAMPLE 7

The polymerization of Example 5 is repeated, except that 2 ml of the catalyst solution are added and 100 ml of 1-hexene were first added to the reactor and 5 bar of ethylene were subsequently added. After 30 minutes, the reactor is vented, the polymerization is stopped using methanol and the polymer is filtered from the suspension, washed with acetone and dried for 12 hours in a vacuum drying oven. This gives 25 g of an ethylene/1-hexene copolymer containing 5.2 mol % of hexene (according to $^{13}$C-NMR) and having an $M_w$ of 60,000 g/mol and an $M_w/M_n$ of 2.6 according to GPC. The DSC melting point of the 2nd heating is 110° C.

EXAMPLE 8

A 1.5 dm$^3$ autoclave, which was thoroughly flushed with ethene beforehand, is charged with 600 cm$^3$ of an 85% strength by weight solution of norbornene in toluene. The solution is saturated with ethene by repeated pressurization with ethene (18 bar). A suspension of 2.28 mg of 4-($\eta^5$-cyclopentadienyl)-4,7,7-trimethyl-($\eta^5$-4,5,6,7-tetrahydroindenyl)$Zr^+CH_2CHCHCH_2B^-(C_6F_5)_3$ in 10 ml of toluene was added to the reactor thus prepared (in the case of hydrogen regulation, hydrogen can be injected at this point). Polymerization was carried out for one hour while stirring, with the ethene pressure being kept at 18 bar by metering in further amounts.

After the end of the reaction time, the polymerization mixture was drained into a vessel and immediately introduced into 5 dm$^3$ of acetone, the mixture was stirred for 10 min and the precipitated product was subsequently filtered off. The filter cake was washed alternately three times each with 10% strength hydrochloric acid and acetone. It was subsequently washed to neutrality with water, the residue was slurried in acetone and filtered again. The polymer thus purified was dried at 80° C. for 15 hours in vacuo (0.2 bar). After drying, there were obtained 224 g of colorless polymer which had a glass transition temperature of 179° C., a viscosity number of 52 cm$^3$/g, a tensile strength of 59 MPa and an elongation at break of 3.1%. The activity was 80.5 kg of polymer/h×mmol.

EXAMPLE 9

106 mg (0.385 mmol) of biscyclopentadienylzirconium ($\eta^4$-butadiene) were dissolved in toluene and admixed with a solution of 186 mg (0.363 mmol) of $B(C_6F_5)_3$ in toluene. The formation of the catalyst can be recognized by the appearance of turbidity or of a precipitate. In parallel thereto, a dry 16 dm$^3$ reactor was flushed first with nitrogen and subsequently with propylene and then charged with 10 dm$^3$ of liquid propylene. 15 cm$^3$ of triisobutylaluminum (20% strength in hydrocarbon, 12 mmol) were then added to the reactor and the mixture was stirred at 30° C. for 15 minutes. The catalyst suspension was subsequently added to the reactor, heated to the polymerization temperature of 70° C.(4° C./min) and the polymerization system was held for 1 hour at 70° C. by means of cooling. The polymerization was stopped by addition of 20 ml of isopropanol. The excess monomer was vented and residues of solvent were taken off in vacuo. This gave 850 g of liquid, atactic polypropylene. The catalyst activity was 8 kg of PP/(g of metallocene×h).

VN=5 cm$^3$/g, $M_w$=1500 g/mol, $M_w/M_n$=3.2.

EXAMPLE 10

10 mg (17.9 $\mu$mol) of rac-dimethylsilanediylbis(2-methyl-4,5-benzo-1-indenyl)zirconium($\eta^4$-butadiene) were dissolved in 10 ml of toluene and admixed with 10 ml of a solution of 9.2 mg (18 mmol) of $B(C_6F_5)_3$ in toluene. The formation of the catalyst can be recognized by the appearance of turbidity or of a dark precipitate. The polymerization was carried out by a method similar to Example 9 at 70° C. The excess monomer was vented and the polymer powder was dried in vacuo. This gave 2500 g of isotactic polypropylene powder.

The catalyst activity was 250 kg of PP/(g of metallocene× h).

VN=240 cm$^3$/g, mp.=148.7° C., $M_w$=298,000 g/mol, $M_w/M_n$=2.2, $MFI_{(230/2.16)}$=3.2 dg/min.

EXAMPLE 11

The preparation of the catalyst suspension from Example 10 was repeated, except that 3 mg (4.8 $\mu$mol) of rac-dimethylsilanediylbis(2-methyl-4-phenyl-1-indenyl)zirconium($\eta^4$-butadiene) dissolved in 10 cm$^3$ of toluene were reacted with 2.5 mg (4.9 $\mu$mol) of $B(C_6F_5)_3$ dissolved in 10 cm$^3$ of toluene. The polymerization was carried out at 60° C. after adding the catalyst suspension to the reactor. The polymerization gave 2250 g of isotactic polypropylene powder.

The catalyst activity was 750 kg of PP/(g of metallocene× h).

VN=620 cm$^3$/g, mp.=155° C., $MFI_{(230/5)}$=0.35 dg/min.

EXAMPLE 12

The preparation of the catalyst suspension from Example 10 was repeated, except that 10 mg (21 $\mu$mol) of rac-dimethylsilanediylbis(2-methyl-1-indenyl)zirconium($\eta^4$-butadiene) dissolved in 10 cm$^3$ of toluene were reacted with 10.7 mg (21 $\mu$mol) of $B(C_6F_5)_3$ dissolved in 10 cm$^3$ of toluene. The polymerization gave 1900 g of isotactic polypropylene powder. The catalyst activity was 190 kg of PP/(g of metallocene×h).

VN=180 cm$^3$/g, mp.=145° C., $M_w$=192,000, $M_w/M_n$=2.2, $MFI_{(230/2.16)}$=12 dg/min.

EXAMPLE 13

The preparation of the catalyst suspension from Example 10 was repeated, except that 10 mg (20.2 $\mu$mol) of phenylmethylmethylenefluorenylcyclopentadienyl-zirconium-($\eta^4$-butadiene) dissolved is 10 cm$^3$ of toluene were reacted with 10.7 mg (21 $\mu$mol) of $B(C_6F_5)_3$ dissolved in 10 cm$^3$ of toluene. The polymerization gave 1100 g of syndiotactic polypropylene powder.

The catalyst activity was 110 kg of PP/(g of metallocene× h).

VN=137 cm$^3$/g, mp.=133° C., $M_w$=122,000 g/mol, $M_w/M_n$=2.3.

EXAMPLE 14

Reactor Preparation

A 1500 ml reactor which had been repeatedly flushed with nitrogen was charged with 1000 ml of an 85% strength by weight solution of norbornene in toluene and the solution was heated to 70° C. The solution was saturated with ethylene by repeated pressurization with ethylene (16 bar gauge pressure). 2 ml of a 20% strength triethylaluminum solution in toluene were added to the depressurized reactor in a countercurrent of ethylene and the mixture was subsequently stirred for 15 minutes.

Catalyst Preparation

A solution of 12.6 mg of tris(pentafluorophenyl)borane (0.025 mmol) in 1.26 ml of toluene was added to the solution of 9.0 mg of (butadiene)isopropylene(1-indenyl)cyclopentadienylzirconium (0.025 mmol) in 0.9 ml of toluene. The catalyst mixture was preactivated for 25 minutes at room temperature.

Polymerization and Isolation

The catalyst mixture was added to the prepared reaction solution and an ethylene pressure of 16 bar was subsequently applied as quickly as possible. Polymerization was carried out for 2 hours at 70° C. while stirring at about 750 rpm, with the ethylene pressure being kept constant at 16 bar.

To end the reaction, the reactor was first vented and the reaction solution was subsequently drained into a vessel. The polymer was precipitated in 2500 ml of acetone and filtered after stirring for 5 minutes. The filter cake was repeatedly washed alternately with 10% strength hydrochloric acid and acetone. It was subsequently washed to neutrality with water and, after addition of 1000 ml of acetone, filtered. The powder thus purified was dried for 15 hours at 80° C. at a pressure of 0.2 bar.

Characterization

After drying, 30 g of colorless powder were obtained; this corresponds to an activity of 610 g of polymer/h×mmol of metallocene. A viscosity number of 106 cm$^3$/g and a glass transition temperature of 135° C. were measured on the polymer. No melting point was able to be detected by means of thermal analysis.

EXAMPLE 15

30 mg (31 μmol) of rac-dimethylsilanediylbis(2-methyl-1-indenyl)Zr$^+$CH$_2$CHCHCH$_2$B$^-$(C$_6$F$_5$)$_3$ are dissolved in 30 ml of toluene. 10 g of SiO$_2$ are stirred into the catalyst solution until a homogeneous distribution is achieved.

The solid is then filtered off from the solvent and washed twice with 10 ml of toluene.

In parallel thereto, a dry 16 dm$^3$ reactor was flushed first with nitrogen and subsequently with propylene and charged with 10 dm$^3$ of liquid propylene. 15 cm$^3$ of triisobutylaluminum (20% strength in hydrocarbon, 12 mmol) were then added to the reactor and the mixture was stirred at 30° C. for 15 minutes. The catalyst suspension was subsequently added to the reactor, heated to the polymerization temperature of 70° C. (4° C./min) and the polymerization system was held at 70° C. for 1 hour by cooling. The polymerization was stopped by addition of 20 ml of isopropanol. The excess monomer was vented and solvent residues were taken off in vacuo.

The polymerization gives 2.5 kg of isotactic polypropylene powder. The catalyst activity was 83 kg of PP/(g of metallocene×h).

VN=184 cm$^3$/g, mp.=145° C., M$_w$=193,000 g/mol, M$_w$/M$_n$=2.2.

The reactor shows no deposits on walls or stirrer.

EXAMPLE 16 a) Preparation of the Catalyst Component

A solution of 1 μmol of biscyclopentadienylzirconium (η$^4$-butadiene) in 1 ml of toluene is admixed with a solution of 1 μmol of tris(pentafluorophenyl)borane in 10 ml of toluene and, after a reaction time of 15 minutes, evaporated in vacuo to a volume of 2 ml. In parallel thereto, 4 g of $^R$Accurel LDPE powder in a sieve fraction of smaller than 200 μm are dried in vacuo and flushed with argon. The support powder is stirred into the catalyst solution until a homogeneous distribution is achieved.

b) Polymerization

A dry 1.5 dm$^3$ stirred reactor is flushed with nitrogen to remove the oxygen and charged with 0.9 dm$^3$ of an inert diesel oil (bp. from 100 to 120° C.). After flushing with ethylene, it is heated to 70° C. and the catalyst is added as powder. Polymerization is subsequently carried out without additional activator at a pressure of 7 bar of ethylene. After 1 hour, the reactor is vented, the polymer is filtered from the suspension and dried for 12 hours in a vacuum drying oven. This gives 18 g of polyethylene powder having a bulk density of 0.253 kg/dm$^3$ and a viscosity number VN of 389 cm$^3$/g. The polydispersity M$_w$/M$_n$ is 2.6 (according to GPC). The reactor shows no deposits on walls or stirrer.

EXAMPLE 17 a) Preparation of the Catalyst Component

Biscyclopentadienyl Zr$^+$CH$_2$CHCHCH$_2$B$^-$(C$_6$F$_5$)$_3$ was supported on SiO$_2$ using a method similar to Example 15.

b) Gas-Phase Polymerization of Ethylene

A gas-phase polymerization of ethylene was carried out in a 2 dm$^3$ steel autoclave having polished walls. The fluidized bed was generated mechanically by means of a double-helix stirrer going around the wall, using an initial charge of 10 g of polyethylene powder as seed bed. Via a pressure burette, first the cocatalyst (2 mmol) of triisobutylaluminum in 2 cm$^3$ of isopentane and subsequently 1 g of the catalyst mixture (19.2 μmol of Zr) were metered in. The polymerization was subsequently carried out at 8 bar partial pressure of ethylene at a temperature of 80° C. for 1 hour and ended by venting the autoclave.

This gave 118 g of polyethylene having a VN of 309 ml/g, corresponding to an activity of 6.2 kg of PE/mmol of metallocene.

EXAMPLE 18

The preparation of the catalyst suspension of Example 10 was repeated, except that 10 mg (24 μmol) of dimethylmethylene-9-fluorenylcyclopentadienylzirconium (4-butadiene) dissolved in 10 cm$^3$ of toluene were reacted with 12.8 mg (25 μmol) of B(C$_6$F$_5$)$_3$ dissolved in 10 cm$^3$ of toluene. The polymerization was carried out after metering the catalyst suspension into the reactor at 60° C. The polymerization gave 900 g of syndiotactic polypropylene powder. The catalyst activity was 90 kg of PP/(g of metallocene×h).

VN=92 cm$^3$/g, m.p.=126° C., M$_w$=63,000 g/mol, M$_w$/M$_n$=2.1

EXAMPLE 19

The preparation of the catalyst suspension of Example 10 was repeated, except that 5 mg (8 μmol) of rac-dimethylsilanediylbis(2-methyl-4,6-diisopropyl-1-indenyl)zirconium(4-butadiene) dissolved in 10 cm$^3$ of toluene were reacted with 4.1 mg (8.1 μmol) of B(C$_6$F$_5$)$_3$ dissolved in 10 cm$^3$ of toluene. The polymerization was carried out after metering the catalyst suspension into the reactor at 60° C. The polymerization gave 2100 g of isotactic polypropylene powder.

The catalyst activity was 420 kg of PP/(g of metallocene×h).

VN=423 cm$^3$/g, mp.=154° C., MFI$_{(230/5)}$=3.1 dg/min, M$_w$=588,000 g/mol, M$_w$/M$_n$=3.5.

EXAMPLE 20

The preparation of the catalyst suspension of Example 11 was repeated. The polymerization was carried out after metering the catalyst suspension into the reactor at 70° C. The polymerization gave 2800 g of isotactic polypropylene powder.

The catalyst activity was 933 kg of PP/(g of metallocene×h).

VN=544 cm$^3$/g, mp.=154° C., MFI$_{(230/5)}$=1.3 dg/min, M$_w$=741,000 g/mol, M$_w$/M$_n$=2.8.

EXAMPLE 21

The preparation of the catalyst suspension of Example 12 was repeated, except that the 16 dm$^3$ reactor was charged with 10 dm³ of liquid propylene and 2.5 standard 1 of hydrogen gas. 10 cm³ of triisobutylaluminum (20% in hydrocarbon, 10 mmol) were then added to the reactor and the mixture was stirred at 30° C. for 15 minutes. The catalyst suspension was subsequently added to the reactor, heated to the polymerization temperature of 70° C. (4° C./min) and the polymerization system was kept at 70° C. for 1 hour by cooling. The polymerization gave 3200 g of isotactic polypropylene powder.

The catalyst activity was 320 kg of PP/(g of metallocene×h).

VN=164 cm³/g, mp.=147° C., $MFI_{(230/2.16)}$=25 dg/min.

EXAMPLE 22

The preparation of the catalyst suspension of Example 10 was repeated, except that 2 mg (3.1 µmol) of rac-dimethylsilanediylbis(2-ethyl-4-phenyl-1-indenyl) zirconium(4-butadiene) dissolved in 5 cm³ of toluene were reacted with 1.7 mg (3.3 µmol) of $B(C_6F_5)_3$ dissolved in 5 cm³ of toluene. The polymerization gave 2150 g of isotactic polypropylene powder.

The catalyst activity was 1075 kg of PP/(g of metallocene×h).

VN=656 cm³/g, mp.=162° C., $MFI_{(230/5)}$=0.8 dg/min, $M_w$=957,000 g/mol, $M_w/M_n$=3.0.

EXAMPLE 23

The preparation of the catalyst suspension of Example 10 was repeated, except that 2 mg (2.8 µmol) of rac-dimethylsilanediylbis(2-methyl-4-naphthyl-1-indenyl) zirconium(4-butadiene) dissolved in 5 cm³ of toluene were reacted with 1.4 mg (2.8 µmol) of $B(C_6F_5)_3$ dissolved in 5 cm³ of toluene. The polymerization gave 2500 g of isotactic polypropylene powder.

The catalyst activity was 1250 kg of PP/(g of metallocene×h).

VN=777 cm³/g, mp.=163° C., $MFI_{(230/5)}$=0.5 dg/min, $M_w$=1,200,000 g/mol, $M_w/M_n$=3.2.

EXAMPLE 24

10 g of silica gel (Davison 948), which had been conditioned at 800° C., were admixed with 0.5 g of $B(C_6F_5)_3$ dissolved in 15 cm³ of toluene and homogenized. The solvent was taken off in vacuo. This resulted in a free-flowing powder. 200 mg of rac-dimethylsilanediylbis(2-methyl-1-indenyl)zirconium(4-butadiene) (435 µmol) were dissolved in 15 cm³ of toluene and applied in small portions to the intensively stirred, free-flowing powder. The powder acquires an intense dark red color. The toluene was subsequently taken off in vacuo. This resulted in 11.3 g of supported catalyst as free-flowing powder. 1.5 g of the supported catalyst were suspended in 10 ml of hexane and introduced into the polymerization reactor. The polymerization was carried out by a method similar to Example A at 70° C. The excess monomer was drawn off and the polymer powder was dried in vacuo. This gave 2350 g of isotactic polypropylene powder having a bulk density of 0.44 g/ml and a mean particle size of the polymer particles of 650 µm. Analysis of the polymer gave VN=172 cm³/g, mp.=145° C., $M_w$=192,000 g/mol, $M_w/M_n$=2.2, $MFI_{(230/2.16)}$=13 dg/min.

EXAMPLE 25

Comparative Example

The preparation of the catalyst suspension of Example 10 was repeated, except that 5 mg (11.1 µmol) of rac-dimethylsilanediylbis-1-indenylzirconium($\eta^4$-butadiene) dissolved in 10 cm³ of toluene were reacted with 5.7 mg (11.1 µmol) of $B(C_6F_5)_3$ dissolved in 10 cm³ of toluene. The polymerization resulted in 2200 g of isotactic polypropylene powder.

The catalyst activity was 440 kg of PP/(g of metallocene×h).

VN=52 cm³/g, mp.=140° C., $M_w$=49,000 g/mol, $M_w/M_n$=2.2.

16.6 mg (40.7 µmol) of rac-dimethylsilanediylbis-1-indenylzirconiumdimethyl were dissolved in 10 cm³ of toluene and reacted with 21 mg (41 µmol) of $B(C_6F_5)_3$ dissolved in 10 cm³ of toluene. No turbidity or precipitate formation can be observed. The catalyst solution is used for the polymerization as in Example 9. This resulted in 130 g of isotactic polypropylene powder.

The catalyst activity was 8 kg of PP/g(g of metallocene×h).

VN=67 cm³/g, mp.=139.5° C., $M_w$=62,000 g/mol, $M_w/M_n$=2.1.

We claim:

1. A zwitterionic transition metal compound of the formula I

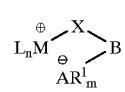

(I)

where

L are identical or different and are each a π-ligand or an electron donor, n is equal to 1, 2, 3 or 4, M is a metal atom of group IIIb, IVb, Vb or VIb of the Periodic Table of the Elements, X is a heteroatom or a hydrocarbon group having 1–40 carbon atoms, X' is a hydrocarbon group having 1–40 carbon atoms, A is an atom of group Ib, IIb, IIIa, IIIb, IVa, Va, Vb, VIb, VIIb or VIIIb of the Periodic Table of the Elements, $R^1$ are identical or different and are each a perhalogenated $C_1$–$C_{40}$-hydrocarbon radical, and m is equal to 1, 2, 3, 4 or 5.

2. A transition metal compound as claimed in claim 1, wherein the radicals L are identical or different and are each a π-ligand.

3. A transition metal compound as claimed in claim 1, wherein the radicals L are identical or different and are each an unsubstituted or substituted cyclopentadienyl group.

4. A transition metal compound as claimed in claim 1, wherein the radicals L are linked to one another via a bridge.

5. A transition metal compound as claimed in claim 1, wherein n=2 when M is a metal atom of group IVb of the Periodic Table of the Elements.

6. A transition metal compound as claimed in claim 1, wherein

M is a metal atom of group IVb of the Periodic Table of the Elements, n is equal to 2, L are identical or different and are each a substituted or unsubstituted cyclopentadienyl group, where two radicals L are optionally linked to one another via a bridge Z and Z is $CR^2R^3$ or $SiR^2R^3$ or a unit Si—$(CR^2R^3)_x$—Si which links two fragments $L_nM^+XX'$—A—$R^1_m$ with one another, where x is an integer from 0 to 10, X and X' together form a three-membered to five-membered hydrocarbon chain which can be saturated or unsaturated and are unsubstituted or substituted by one or more $C_1$–$C_{20}$-hydrocarbon radicals, $R^2$ and $R^3$ are identical or different and are each a hydrogen atom, a halogen atom, a $C_1$–$C_{20}$-alkyl group, a $C_1$–$C_{10}$-fluoralkyl group, a $C_1$–$C_{10}$-alkoxy group, a $C_6$–$C_{14}$-aryl group, a $C_6$–$C_{10}$-fluoroaryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group, or $R^2$ and $R^3$ together with the atoms connected them form one or more rings, and $R^2$ and $R^3$ are optionally bonded to L;

A is an atom of group Ib, IIb, IIIa, IVa, Va, Vb of the Periodic Table of the Elements, $R^1$ are identical or different and are each a perfluorinated alkyl or aryl group having from 1 to 20 carbon atoms and m is equal to 2, 3 or 4.

7. A transition metal compound as claimed in claim 6, wherein

M is zirconium, n is equal to 2,

L are identical or different and are each a substituted cyclopentadienyl group, where two radicals L are linked to one another via a bridge Z, where Z is $CR^2R^3$ or $SiR^2R^3$ and $R^2$ and $R^3$ are as defined in claim 6, X and X' together form an unsaturated four-membered hydrocarbon chain whose hydrogen atoms are optionally replaced by $C_1$–$C_{20}$-alkyl groups, A is boron atom, $R^1$ are identical and are each a pentafluorophenyl group ($C_6F_5$) and m is equal to 3.

8. A catalyst component comprising at least one transition metal compound as claimed in claim 1.

9. A catalyst component as claimed in claim 8, additionally containing a support.

10. A process for preparing a compound according to claim 1 of the formula I,

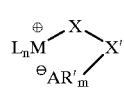
(I)

where

L are identical or different and are each a π ligand or an electron donor, n is equal to 1, 2, 3 or 4, M is a metal atom of group IIIb, IVb, Vb or VIb of the Periodic Table of the Elements, X is a heteroatom or a hydrocarbon group having 1–40 carbon atoms, X' is a hydrocarbon group having 1–40 carbon atoms, A is an atom of group Ib, IIb, IIIa, IIIb, IVa, Va, Vb, VIb, VIIb or VIIIb of the Periodic Table of the Elements, $R^1$ are identical or different and are each a perhalogenated $C_1$–$C_{40}$-hydrocarbon radical, and m is equal to 1, 2, 3, 4 or 5, which comprises reacting a compound of the formula II

II with a compound of the formula III

III and reacting the reaction product with a compound of the formula $AR^1_m$, where L, n, M, X, B, A, $R^1$ and m in the formulae II, III and $AR^1_m$ are as defined for the formula I and Hal is a halogen atom.

11. A zwiterionic transition metal compound of the formula

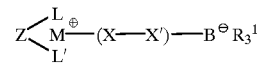

wherein:

L and L' are identical or different and are each a substituted or unsubstituted cyclopentadienyl group;

Z is a bridge linking together said L and L' and is a group of the formula $CR^2R^3$ or $SiR^2R^3$;

$R^2$ and $R^3$ are identical or different and are each a hydrogen atom, a halogen atom, a $C_1$–$C_{20}$-alkyl group, a $C_1$–$C_{10}$-fluoralkyl group, a $C_1$–$C_{10}$-alkoxy group, a $C_6$–$C_{14}$-aryl group, a $C_6$–$C_{10}$-fluoroaryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group, or $R^2$ and $R^3$ together with the atoms connected them form one or more rings, and $R^2$ and $R^3$ are optionally bonded to L;

M is a metal atom of group IVb of the Periodic Table of the Elements;

X–X' is a 3- to 5-membered saturated or unsaturated hydrocarbon chain which is unsubstituted or substituted by one or more $C_1$–$C_{20}$-hydrocarbon radicals; and the $R^1$ radicals are identical or different and are each a perfluorinated alkyl or aryl group having from 1 to 20 carbon atoms.

12. A catalyst system for olefin polymerization comprising a transition metal compound of claim 11 and, optionally, a catalyst support material.

13. A catalyst system as claimed in claim 12, wherein said catalyst system is essentially free of an aluminoxane except when said catalyst support material is present and is a solid aluminoxane.

14. The catalyst as claimed in claim 8, wherein M is titanium, zirconium or hafnium.

15. The catalyst as claimed in claim 12, wherein M is zirconium.

16. The catalyst as claimed in claim 14, wherein an unsubstituted or

M is Zr, n is equal to 2,

L are identical or different and are each a substituted cyclopentadienyl group, where two radicals L are linked to one another via a bridge Z, and Z is $CR^2R^3$ or $SiR^2R^3$ or a unit $Si—(CR^2R^3)_x—Si$ which links two fragments $L_nM^+XX'A—R^1_m$ with one another, where x is an integer from 0 to 10, X and X' together form a three-membered to five-membered ($C_3$–$C_5$)-alkyl chain which is saturated or unsaturated and optionally substituted by $C_1$–$C_{20}$-hydrocarbon radicals, A is a metal of group Ib, IIb, IIIb, IVa, Vb, of the Periodic Table of the Elements, $R^1$ are identical or different and are each a pentafluorinated alkyl or aryl group having from 1 to 20 carbon atoms, $R^2$ and $R^3$ are identical or different and are each a hydrogen atom, a halogen atom, a $C_1$–$C_{20}$-alkyl group, a $C_1$–$C_{10}$-fluoralkyl group, a $C_1$–$C_{10}$-alkoxy group, a $C_6$–$C_{14}$-aryl group, a $C_6$–$C_{10}$-fluoroaryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group and m is equal to 3.

17. The catalyst as claimed in claim 8, wherein

M is zirconium, n is equal to 2,

L are identical or different and are each a substituted cyclopentadienyl group, where two radicals L are bonded to one another via a bridge Z, where Z is $CR^2R^3$ or $SiR^2R^3$, X and X' together form an unsaturated four-membered ($C_4$)-alkyl chain whose hydrogen atoms can also be replaced by $C_1$–$C_{20}$-alkyl groups, A is a boron atom, $R^1$ are identical and are each a pentafluorophenyl group ($C_6F_5$), $R^2$ and $R^3$ are identical or different and are each a hydrogen atom, a halogen atom, a $C_1$–$C_{20}$-alkyl group, a $C_1$–$C_{10}$-fluoralkyl group, a $C_1$–$C_{10}$-alkoxy group, a $C_6$–$C_{14}$-aryl group, a $C_6$–$C_{10}$-fluoroaryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group and m is equal to 3.

18. The compound as claimed in claim 1, wherein the transition metal compound of the formula I is selected from the group consisting of bis(cyclopentadienyl)$Zr^+CH_2CHCHCH_2B^-(C_6F_5)_3$;
bis(methylcyclopentadienyl)$Zr^+CH_2CHCHCH_2B^-(C_6F_5)_3$;
bis(n-butylcyclopentadienyl)$Zr^+CH_2CHCHCH_2B^-(C_6F_5)_3$;
bisindenyl$Zr^+CH_2CHCHCH_2B^-(C_6F_5)_3$;
(tert-butylamido)dimethyl(tetramethyl-$\eta^5$-cyclopentadienyl)silane$Zr^{+CH}{}_2CHCHCH_2B^-(C_6F_5)_3$;
bis(2-methylbenzoindenyl)$Zr^+CH_2CHCHCH_2B^-(C_6F_5)_3$;
dimethylsilanediylbis(2-methylindenyl)$Zr^+CH_2CHCHCH_2B^-(C_6F_5)_3$;
dimethylsilanediylbisindenyl$Zr^+CH_2CHCHCH_2B^-(C_6F_5)_3$;
dimethylsilanediylbis(2-methylbenzoindenyl)$Zr^+CH_2CHCHCH_2B^-(C_6F_5)_3$;
dimethylsilanediyl(2-methylbenzoindenyl)(2-methylindenyl)$Zr^+CH_2CHCHCH_2B^-(C_6F_5)_3$;
dimethylsilanediyl(2-methylbenzoindenyl)(2-methyl-4-phenylindenyl)$Zr^+CH_2CHCHCH_2B^-(C_6F_5)_3$;
dimethylsilanediyl(2-methylindenyl)(4-phenylindenyl)$Zr^+CH_2CHCHCH_2B^-(C_6F_5)_3$;
dimethylsilanediylbis(2-methyl-4-phenylindenyl)$Zr^+CH_2CHCHCH_2B^-(C_6F_5)_3$;
dimethylsilanediylbis(2-methyl-4,6-diisopropylindenyl)$Zr^+CH_2CHCHCH_2B^-(C_6F_5)_3$;
dimethylsilanediylbis(2-methyl-4-naphthylindenyl)$Zr^+CH_2CHCHCH_2B^-(C_6F_5)_3$;
isopropylidene(cyclopentadienyl)(fluorenyl)$Zr^+CH_2CHCHCH_2B^-(C_6F_5)_3$;
isopropylidene(cyclopentadienyl)(indenyl)$Zr^+CH_2CHCHCH_2B^-(C_6F_5)_3$;
[4-$\eta^5$-cyclopentadienyl-4,7,7-trimethyl-($\eta^5$-4,5,6,7-tetrahydroindenyl)$Zr^+CH_2CHCHCH_2B^-(C_6F_5)_3$;
dimethylsilanediylbis(2-methylindenyl)$Zr^+OCH_2CH_2CH_2B^-(C_6F_5)_3$;
dimethylsilanediylbisindenyl$Zr^+OCH_2CH_2CH_2B^-(C_6F_5)_3$;
dimethylsilanediylbis(2-methylbenzoindenyl)$Zr^+OCH_2CH_2CH_2B^-(C_6F_5)_3$;
dimethylsilanediyl(2-methylbenzoindenyl)(2-methylindenyl)$Zr^+OCH_2CH_2CH_2B^-(C_6F_5)_3$;
dimethylsilanediyl(2-methylbenzoindenyl)(2-methyl-4-phenylindenyl)$Zr^+OCH_2CH_2CH_2B^-(C_6F_5)_3$;
dimethylsilanediyl(2-methylindenyl)(4-phenylindenyl)$Zr^+OCH_2CH_2CH_2B^-(C_6F_5)_3$;
dimethylsilanediylbis(2-methyl-4-phenylindenyl)$Zr^+OCH_2CH_2CH_2B^-(C_6F_5)_3$;
dimethylsilanediylbis(2-methyl-4,6-diisopropylindenyl)$Zr^+OCH_2CH_2CH_2B^-(C_6F_5)_3$;
dimethylsilanediylbis(2-methylindenyl)$Zr^+CH_2CHCHCH_2B^-(CF_3)_3$;
dimethylsilanediylbisindenyl$Zr^+CH_2CHCHCH_2B^-(CF_3)_3$;
dimethylsilanediylbis(2-methylbenzoindenyl)$Zr^+CH_2CHCHCH_2B^-(CF_3)_3$;
dimethylsilanediyl(2-methylbenzoindenyl)(2-methylindenyl)$Zr^+CH_2CHCHCH_2B^-(CF_3)_3$;
dimethylsilanediyl(2-methylbenzoindenyl)(2-methyl-4-phenylindenyl)$Zr^+CH_2CHCHCH_2CH_2B^-(CF_3)_3$;
dimethylsilanediyl(2-methylindenyl)(4-phenylindenyl)$Zr^+CH_2CHCHCH_2B^-(CF_3)_3$;
dimethylsilanediylbis(2-methyl-4-phenylindenyl)$Zr^+CH_2CHCHCH_2B^-(CF_3)_3$;
dimethylsilanediylbis(2-methyl-4,6-diisopropylindenyl)$Zr^+CH_2CHCHCH_2B^-(CF_3)_3$;
dimethylsilanediylbis(2-methyl-4-naphthylindenyl)$Zr^+CH_2CHCHCH_2B^-(CF_3)_3$;
dimethylsilanediylbis(2-methylindenyl)$Zr^+CH_2C(CH_3)C(CH_3)CH_2B^-(CF_3)_3$;
dimethylsilanediylbisindenyl$Zr^+CH_2C(CH_3)C(CH_3)CH_2B^-(CF_3)_3$;
dimethylsilanediylbis(2-methylbenzoindenyl)$Zr^+CH_2C(CH_3)C(CH_3)CH_2B^-(CF_3)_3$;
dimethylsilanediyl(2-methylbenzoindenyl)(2-methylindenyl)$Zr^+CH_2C(CH_3)C(CH_3)CH_2B^-(CF_3)_3$;
dimethylsilanediyl(2-methylbenzoindenyl)(2-methyl-4-phenylindenyl)$Zr^+CH_2C(CH_3)C(CH_3)CH_2B^-(CF_3)_3$;
dimethylsilanediyl(2-methylindenyl)(4-phenylindenyl)$Zr^+CH_2C(CH_3)C(CH_3)CH_2B^-(CF_3)_3$;
dimethylsilanediylbis(2-methyl-4-phenylindenyl)$Zr^+CH_2C(CH_3)C(CH_3)CH_2B^-(CF_3)_3$;
dimethylsilanediylbis(2-methyl-4,6-diisopropylindenyl)$Zr^+CH_2C(CH_3)C(CH_3)C_2B^-(CF_3)_3$;
dimethylsilanediylbis(2-methyl-4-naphthylindenyl)$Zr^+CH_2C(CH_3)C(CH_3)CH_2B^-(CF_3)_3$;
methylphenylmethylene(fluorenyl)(cyclopentadienyl)$Zr^+CH_2CHCHCH_2B^-(C_6F_5)_3$;
diphenylmethylene(fluorenyl)(cyclopentadienyl)$Zr^+CH_2CHCHCH_2B^-(C_6F_5)_3$;
isopropylidene(3-methylcyclopentadienyl)(fluorenyl)$Zr^+CH_2CHCHCH_2B^-(C_6F_5)_3$;
dimethylsilanediyl(3-tert-butylcyclopentadienyl)(fluorenyl)$Zr^+CH_2CHCHCH_2B^-(C_6F_5)_3$;
diphenylsilanediyl(3-(trimethylsilyl)cyclopentadienyl)(fluorenyl)$Zr^+CH_2CHCHCH_2B^-(C_6F_5)_3$;
phenylmethylsilanediylbis(2-methylindenyl)$Zr^+CH_2CHCHCH_2B^-(C_6F_5)_3$;
phenylmethylsilanediylbisindenyl$Zr^+CH_2CHCHCH_2B^-(C_6F_5)_3$;

phenylmethylsilanediylbis(2-methyl-4,5-benzoindenyl)Zr$^+$CH$_2$CHCHCH$_2$B$^-$(C$_6$F$_5$)$_3$;
phenylmethylsilanediyl(2-methyl-4,5-benzoindenyl)(2-methylindenyl)Zr$^+$CH$_2$CHCHCH$_2$B$^-$(C$_6$F$_5$)$_3$;
phenylmethylsilanediyl(2-methyl-4,5-benzoindenyl)(2-methyl-4-phenylindenyl)Zr$^+$CH$_2$CHCHCH$_2$B$^-$(C$_6$F$_5$)$_3$;
phenylmethylsilanediyl(2-methylindenyl)(4-phenylindenyl)Zr$^+$CH$_2$CHCHCH$_2$B$^-$(C$_6$F$_5$)$_3$;
phenylmethylsilanediylbis(2-methyl-4-phenylindenyl)Zr$^+$CH$_2$CHCHCH$_2$B$^-$(C$_6$F$_5$)$_3$;
phenylmethylsilanediylbis(2-ethyl-4-phenylindenyl)Zr$^+$CH$_2$CHCHCH$_2$B$^-$(C$_6$F$_5$)$_3$;
phenylmethylsilanediylbis(2-methyl-4,6-diisopropylindenyl)Zr$^+$CH$_2$CHCHCH$_2$B$^-$(C$_6$F$_5$)$_3$;
phenylmethylsilanediylbis(2-methyl-4-naphthylindenyl)Zr$^+$CH$_2$CHCHCH$_2$B$^-$(C$_6$F$_5$)$_3$;
ethylenebis(2-methylindenyl)Zr$^+$CH$_2$CHCHCH$_2$B$^-$(C$_6$F$_5$)$_3$;
ethylenebisindenylZr$^+$CH$_2$CHCHCH$_2$B$^-$(C$_6$F$_5$)$_3$;
ethylenebis(2-methyl-4,5-benzoindenyl)Zr$^+$CH$_2$CHCHCH$_2$B$^-$(C$_6$F$_5$)$_3$;
ethylene(2-methyl-4,5-benzoindenyl)(2-methylindenyl)Zr$^+$CH$_2$CHCHCH$_2$B$^-$(C$_6$F$_5$)$_3$;
ethylene(2-methyl-4,5-benzoindenyl)(2-methyl-4-phenylindenyl)Zr$^+$CH$_2$CHCHCH$_2$B$^-$(C$_6$F$_5$)$_3$;
ethylene(2-methylindenyl)(4-phenylindenyl)Zr$^+$CH$_2$CHCHCH$_2$B$^-$(C$_6$F$_5$)$_3$;
ethylenebis(2-methyl-4,5-benzoindenyl)Zr$^+$CH$_2$CHCHCH$_2$B$^-$(C$_6$F$_5$)$_3$;
ethylenebis(2-methyl-4-phenylindenyl)Zr$^+$CH$_2$CHCHCH$_2$B$^-$(C$_6$F$_5$)$_3$;
ethylenebis(2-methyl-4,6-diisopropylindenyl)Zr$^+$CH$_2$CHCHCH$_2$B$^-$(C$_6$F$_5$)$_3$;
ethylenebis(2-methyl-4-naphthylindenyl)Zr$^+$CH$_2$CHCHCH$_2$B$^-$(C$_6$F$_5$)$_3$;
ethylenebis(2-ethyl-4-phenylindenyl)Zr$^+$CH$_2$CHCHCH$_2$B$^-$(C$_6$F$_5$)$_3$;
ethylenebis(2-ethyl-4,6-diisopropylindenyl)Zr$^+$CH$_2$CHCHCH$_2$B$^-$(C$_6$F$_5$)$_3$;
ethylenebis(2-ethyl-4-naphthylindenyl)Zr$^+$CH$_2$CHCHCH$_2$B$^-$(C$_6$F$_5$)$_3$;
dimethylsilanediylbis(2-ethyl-4-phenylindenyl)Zr$^+$CH$_2$CHCHCH$_2$B$^-$(C$_6$F$_5$)$_3$;
dimethylsilanediylbis(2,3,5-trimethylcyclopentadienyl)Zr$^+$CH$_2$CHCHCH$_2$B$^-$(C$_6$F$_5$)$_3$;
1,6-{bis[methylsilylbis(2-methyl-4-phenylindenyl)Zr$^+$CH$_2$CHCHCH$_2$B$^-$(C$_6$F$_5$)$_3$]}hexane;
1,6-{bis[methylsilylbis(2-ethyl-4-phenylindenyl)Zr$^+$CH$_2$CHCHCH$_2$B$^-$(C$_6$F$_5$)$_3$]}hexane;
1,6-{bis[methylsilylbis(2-methyl-4-naphthylindenyl)Zr$^+$CH$_2$CHCHCH$_2$B$^-$(C$_6$F$_5$)$_3$]}hexane;
1,6-{bis[methylsilylbis(2-methyl-4,5-benzoindenyl)Zr$^+$CH$_2$CHCHCH$_2$B$^-$(C$_6$F$_5$)$_3$]}hexane;
1,6-{bis[methylsilyl(2-methyl-4-phenylindenyl)(2-methylindenyl)Zr$^+$CH$_2$CHCHCH$_2$B$^-$(C$_6$F$_5$)$_3$]}hexane;
1,2-{bis[methylsilylbis(2-methyl-4-phenylindenyl)Zr$^+$CH$_2$CHCHCH$_2$B$^-$(C$_6$F$_5$)$_3$]}ethane;
1,2-{bis[methylsilylbis(2-ethyl-4-phenylindenyl)Zr$^+$CH$_2$CHCHCH$_2$B$^-$(C$_6$F$_5$)$_3$]}ethane;
1,2-{bis[methylsilylbis(2-methyl-4-naphthylindenyl)Zr$^+$CH$_2$CHCHCH$_2$B$^-$(C$_6$F$_5$)$_3$]}ethane;
1,2-{bis[methylsilylbis(2-methyl-4,5-benzoindenyl)Zr$^+$CH$_2$CHCHCH$_2$B$^-$(C$_6$F$_5$)$_3$]}ethane; and
1,2-{bis[methylsilyl(2-methyl-4-phenylindenyl)(2-methylindenyl)Zr$^+$CH$_2$CHCHCH$_2$B$^-$(C$_6$F$_5$)$_3$]}ethane.

19. The catalyst as claimed in claim 8, wherein the transition metal compound of the formula I is selected from the group consisting of bis(cyclopentadienyl)Zr$^+$CH$_2$CHCHCH$_2$B$^-$(C$_6$F$_5$)$_3$;
bis(methylcyclopentadienyl)Zr$^+$C$_2$CHCHCH$_2$B$^-$(C$_6$F$_5$)$_3$;
bis(n-butylcyclopentadienyl)Zr$^+$CH$_2$CHCHCH$_2$B$^-$(C$_6$F$_5$)$_3$;
bisindenylZr$^+$CH$_2$CHCHCH$_2$B$^-$(C$_6$F$_5$)$_3$;
(tert-butylamido)dimethyl(tetramethyl-$\eta^5$-cyclopentadienyl)silaneZr$^+$CH$_2$CHCHCH$_2$B$^-$(C$_6$F$_5$)$_3$;
bis(2-methylbenzoindenyl)Zr$^+$CH$_2$CHCHCH$_2$B$^-$(C$_6$F$_5$)$_3$;
dimethylsilanediylbis(2-methylindenyl)Zr$^+$CH$_2$CHCHCH$_2$B$^-$(C$_6$F$_5$)$_3$;
dimethylsilanediylbisindenylZr$^+$CH$_2$CHCHCH$_2$B$^-$(C$_6$F$_5$)$_3$;
dimethylsilanediylbis(2-methylbenzoindenyl)Zr$^+$CH$_2$CHCHCH$_2$B$^-$(C$_6$F$_5$)$_3$;
dimethylsilanediyl(2-methylbenzoindenyl)(2-methylindenyl)Zr$^+$CH$_2$CHCHCH$_2$B$^-$(C$_6$F$_5$)$_3$;
dimethylsilanediyl(2-methylbenzoindenyl)(2-methyl-4-phenylindenyl)Zr$^+$CH$_2$CHCHCH$_2$B$^-$(C$_6$F$_5$)$_3$;
dimethylsilanediyl(2-methylindenyl)(4-phenylindenyl)Zr$^+$CH$_2$CHCHCH$_2$B$^-$(C$_6$F$_5$)$_3$;
dimethylsilanediylbis(2-methyl-4-phenylindenyl)Zr$^+$CH$_2$CHCHCH$_2$B$^-$(C$_6$F$_5$)$_3$;
dimethylsilanediylbis(2-methyl-4,6-diisopropylindenyl)Zr$^+$CH$_2$CHCHCH$_2$B$^-$(C$_6$F$_5$)$_3$;
dimethylsilanediylbis(2-methylbenzoindenyl)Zr$^+$CH$_2$CHCHCH$_2$B$^-$(CF$_3$)$_3$;
dimethylsilanediyl(2-methylbenzoindenyl)(2-methylindenyl)Zr$^+$CH$_2$CHCHCH$_2$B$^-$(CF$_3$)$_3$;
dimethylsilanediyl(2-methylbenzoindenyl)(2-methyl-4-phenylindenyl)Zr$^+$CH$_2$CHCHCH$_2$B$^-$(CF$_3$)$_3$;
dimethylsilanediyl(2-methylindenyl)(4-phenylindenyl)Zr$^+$CH$_2$CHCHCH$_2$B$^-$(CF$_3$)$_3$;
dimethylsilanediylbis(2-methyl-4-phenylindenyl)Zr$^+$CH$_2$CHCHCH$_2$B$^-$(CF$_3$)$_3$;
dimethylsilanediylbis(2-methyl-4,6-diisopropylindenyl)Zr$^+$CH$_2$CHCHCH$_2$B$^-$(CF$_3$)$_3$;
dimethylsilanediylbis(2-methyl-4-naphthylindenyl)Zr$^+$CH$_2$CHCHCH$_2$B$^-$(CF$_3$)$_3$;
dimethylsilanediylbis(2-methylindenyl)Zr$^+$CH$_2$C(CH$_3$)C(CH$_3$)CH$_2$B$^-$(CF$_3$)$_3$;
dimethylsilanediylbisindenylZr$^+$CH$_2$C(CH$_3$)C(CH$_3$)CH$_2$B$^-$(CF$_3$)$_3$;
dimethylsilanediylbis(2-methylbenzoindenyl)Zr$^+$CH$_2$C(CH$_3$)C(CH$_3$)CH$_2$B$^-$(CF$_3$)$_3$;
dimethylsilanediyl(2-methylbenzoindenyl)(2-methylindenyl)Zr$^+$CH$_2$C(CH$_3$)C(CH$_3$)CH$_2$B$^-$(CF$_3$)$_3$;
dimethylsilanediyl(2-methylbenzoindenyl)(2-methyl-4-phenylindenyl)Zr$^+$CH$_2$C(CH$_3$)C(CH$_3$)CH$_2$B$^-$(CF$_3$)$_3$;
dimethylsilanediyl(2-methylindenyl)(4-phenylindenyl)Zr$^+$CH$_2$C(CH$_3$)C(CH$_3$)CH$_2$B$^-$(CF$_3$)$_3$;
dimethylsilanediylbis(2-methyl-4-naphthylindenyl)Zr$^+$CH$_2$CHCHCH$_2$B$^-$(C$_6$F$_5$)$_3$;
isopropylidene(cyclopentadienyl)(fluorenyl)Zr$^+$CH$_2$CHCHCH$_2$B$^-$(C$_6$F$_5$)$_3$;
isopropylidene(cyclopentadienyl)(indenyl)Zr$^+$CH$_2$CHCHCH$_2$B$^-$(C$_6$F$_5$)$_3$;
[4-$\eta^5$-cyclopentadienyl-4,7,7-trimethyl-($\eta^5$-4,5,6,7-tetrahydroindenyl)Zr$^+$CH$_2$CHCHCH$_2$B$^-$(C$_6$F$_5$)$_3$;
dimethylsilanediylbis(2-methylindenyl)Zr$^+$OCH$_2$CH$_2$CH$_2$B$^-$(C$_6$F$_5$)$_3$;
dimethylsilanediylbisindenylZr$^+$OCH$_2$CH$_2$C$_2$B$^-$(C$_6$F$_5$)$_3$;
dimethylsilanediylbis(2-methylbenzoindenyl)Zr$^+$OCH$_2$CH$_2$CH$_2$B$^-$(C$_6$F$_5$)$_3$;
dimethylsilanediyl(2-methylbenzoindenyl)(2-methylindenyl)Zr$^+$OCH$_2$CH$_2$CH$_2$B$^-$(C$_6$F$_5$)$_3$;
dimethylsilanediyl(2-methylbenzoindenyl)(2-methyl-4-phenylindenyl)Zr$^+$OCH$_2$CH$_2$CH$_2$B$^-$(C$_6$F$_5$)$_3$;
dimethylsilanediyl(2-methylindenyl)(4-phenylindenyl)Zr$^+$OCH$_2$CH$_2$CH$_2$B$^-$(C$_6$F$_5$)$_3$;

dimethylsilanediylbis(2-methyl-4-phenylindenyl)Zr$^+$OCH$_2$CH$_2$CH$_2$B$^-$(C$_6$F$_5$)$_3$;
dimethylsilanediylbis(2-methyl-4,6-diisopropylindenyl)Zr$^+$OCH$_2$CH$_2$CH$_2$B$^-$(C$_6$F$_5$)$_3$;
dimethylsilanediylbis(2-methylindenyl)Zr$^+$CH$_2$CHCHCH$_2$B$^-$(CF$_3$)$_3$;
dimethylsilanediylbisindenylZr$^+$CH$_2$CHCHCH$_2$B$^-$(CF$_3$)$_3$;
dimethylsilanediylbis(2-methyl-4-phenylindenyl)Zr$^+$CH$_2$C(CH$_3$)C(CH$_3$)CH$_2$B$^-$(CF$_3$)$_3$;
dimethylsilanediylbis(2-methyl-4,6-diisopropylindenyl)Zr$^+$CH$_2$C(CH$_3$)C(CH$_3$)CH$_2$B$^-$(CF$_3$)$_3$;
dimethylsilanediylbis(2-methyl-4-naphthylindenyl)Zr$^+$CH$_2$C(CH$_3$)C(CH$_3$)CH$_2$B$^-$(CF$_3$)$_3$;
methylphenylmethylene(fluorenyl)(cyclopentadienyl)Zr$^+$CH$_2$CHCHCH$_2$B$^-$(C$_6$F$_5$)$_3$;
diphenylmethylene(fluorenyl)(cyclopentadienyl)Zr$^+$CH$_2$CHCHCH$_2$B$^-$(C$_6$F$_5$)$_3$;
isopropylidene(3-methylcyclopentadienyl)(fluorenyl)Zr$^+$CH$_2$CHCHCH$_2$B$^-$(C$_6$F$_5$)$_3$;
dimethylsilanediyl(3-tert-butylcyclopentadienyl)(fluorenyl)Zr$^+$CH$_2$CHCHCH$_2$B$^-$(C$_6$F$_5$)$_3$;
diphenylsilanediyl(3-(trimethylsilyl)cyclopentadienyl)(fluorenyl)Zr$^+$CH$_2$CHCHCH$_2$B$^-$(C$_6$F$_5$)$_3$;
phenylmethylsilanediylbis(2-methylindenyl)Zr$^+$CH$_2$CHCHCH$_2$B$^-$(C$_6$F$_5$)$_3$;
phenylmethylsilanediylbisindenylZr$^+$CH$_2$CHCHCH$_2$B$^-$(C$_6$F$_5$)$_3$;
phenylmethylsilanediylbis(2-methyl-4,5-benzoindenyl)Zr$^+$CH$_2$CHCHCH$_2$B$^-$(C$_6$F$_5$)$_3$;
phenylmethylsilanediyl(2-methyl-4,5-benzoindenyl)(2-methylindenyl)Zr$^+$CH$_2$CHCHCH$_2$B$^-$(C$_6$F$_5$)$_3$;
phenylmethylsilanediyl(2-methyl-4,5-benzoindenyl)(2-methyl-4-phenylindenyl)Zr$^+$CH$_2$CHCHCH$_2$B$^-$(C$_6$F$_5$)$_3$;
phenylmethylsilanediyl(2-methylindenyl)(4-phenylindenyl)Zr$^+$CH$_2$CHCHCH$_2$B$^-$(C$_6$F$_5$)$_3$;
phenylmethylsilanediylbis(2-methyl-4-phenylindenyl)Zr$^+$CH$_2$CHCHCH$_2$B$^-$(C$_6$F$_5$)$_3$;
phenylmethylsilanediylbis(2-ethyl-4-phenylindenyl)Zr$^+$CH$_2$CHCHCH$_2$B$^-$(C$_6$F$_5$)$_3$;
phenylmethylsilanediylbis(2-methyl-4,6-diisopropylindenyl)Zr$^+$CH$_2$CHCHCH$_2$B$^-$(C$_6$F$_5$)$_3$;
phenylmethylsilanediylbis(2-methyl-4-naphthylindenyl)Zr$^+$CH$_2$CHCHCH$_2$B$^-$(C$_6$F$_5$)$_3$;
ethylenebis(2-methylindenyl)Zr$^+$CH$_2$CHCHCH$_2$B$^-$(C$_6$F$_5$)$_3$;
ethylenebisindenylZr$^+$CH$_2$CHCHCH$_2$B$^-$(C$_6$F$_5$)$_3$;
ethylenebis(2-methyl-4,5-benzoindenyl)Zr$^+$CH$_2$CHCHCH$_2$B$^-$(C$_6$F$_5$)$_3$;
ethylene(2-methyl-4,5-benzoindenyl)(2-methylindenyl)Zr$^+$CH$_2$CHCHCH$_2$B$^-$(C$_6$F$_5$)$_3$;
ethylene(2-methyl-4,5-benzoindenyl)(2-methyl-4-phenylindenyl)Zr$^+$CH$_2$CHCHCH$_2$B$^-$(C$_6$F$_5$)$_3$;
ethylene(2-methylindenyl)(4-phenylindenyl)Zr$^+$CH$_2$CHCHCH$_2$B$^-$(C$_6$F$_5$)$_3$;
ethylenebis(2-methyl-4,5-benzoindenyl)Zr$^+$CH$_2$CHCHCH$_2$B$^-$(C$_6$F$_5$)$_3$;
ethylenebis(2-methyl-4-phenylindenyl)Zr$^+$CH$_2$CHCHCH$_2$B$^-$(C$_6$F$_5$)$_3$;
ethylenebis(2-methyl-4,6-diisopropylindenyl)Zr$^+$CH$_2$CHCHCH$_2$B$^-$(C$_6$F$_5$)$_3$;
ethylenebis(2-methyl-4-naphthylindenyl)Zr$^+$CH$_2$CHCHCH$_2$B$^-$(C$_6$F$_5$)$_3$;
ethylenebis(2-ethyl-4-phenylindenyl)Zr$^+$CH$_2$CHCHCH$_2$B$^-$(C$_6$F$_5$)$_3$;
ethylenebis(2-ethyl-4,6-diisopropylindenyl)Zr$^+$CH$_2$CHCHCH$_2$B$^-$(C$_6$F$_5$)$_3$;
ethylenebis(2-ethyl-4-naphthylindenyl)Zr$^+$CH$_2$CHCHCH$_2$B$^-$(C$_6$F$_5$)$_3$;
dimethylsilanediylbis(2-ethyl-4-phenylindenyl)Zr$^+$CH$_2$CHCHCH$_2$B$^-$(C$_6$F$_5$)$_3$;
dimethylsilanediylbis(2,3,5-trimethylcyclopentadienyl)Zr$^+$CH$_2$CHCHCH$_2$B$^-$(C$_6$F$_5$)$_3$;
1,6-{bis[methylsilylbis(2-methyl-4-phenylindenyl)Zr$^+$CH$_2$CHCHCH$_2$B$^-$(C$_6$F$_5$)$_3$]}hexane;
1,6-{bis[methylsilylbis(2-ethyl-4-phenylindenyl)Zr$^+$CH$_2$CHCHCH$_2$B$^-$(C$_6$F$_5$)$_3$]}hexane;
1,6-{bis[methylsilylbis(2-methyl-4-naphthylindenyl)Zr$^+$CH$_2$CHCHCH$_2$B$^-$(C$_6$F$_5$)$_3$]}hexane;
1,6-{bis[methylsilylbis(2-methyl-4,5-benzoindenyl)Zr$^+$CH$_2$CHCHCH$_2$B$^-$(C$_6$F$_5$)$_3$]}hexane;
1,6-{bis[methylsilyl(2-methyl-4-phenylindenyl)(2-methylindenyl)Zr$^+$CH$_2$CHCHCH$_2$B$^-$(C$_6$F$_5$)$_3$]}hexane;
1,2-{bis[methylsilylbis(2-methyl-4-phenylindenyl)Zr$^+$CH$_2$CHCHCH$_2$B$^-$(C$_6$F$_5$)$_3$]}ethane;
1,2-{bis[methylsilylbis(2-ethyl-4-phenylindenyl)Zr$^+$CH$_2$CHCHCH$_2$B$^-$(C$_6$F$_5$)$_3$]}ethane;
1,2-{bis[methylsilylbis(2-methyl-4-naphthylindenyl)Zr$^+$CH$_2$CHCHCH$_2$B$^-$(C$_6$F$_5$)$_3$]}ethane;
1,2-{bis[methylsilylbis(2-methyl-4,5-benzoindenyl)Zr$^+$CH$_2$CHCHCH$_2$B$^-$(C$_6$F$_5$)$_3$]}ethane; and
1,2-{bis[methylsilyl(2-methyl-4-phenylindenyl)(2-methylindenyl)Zr$^+$CH$_2$CHCHCH$_2$B$^-$(C$_6$F$_5$)$_3$]}ethane.

20. The compound as claimed in claim 1, wherein M is zirconium.

21. The compound as claimed in claim 1, wherein M is a metal atom group IVb of the Periodic Table of Elements.

* * * * *